(12) United States Patent
Kladders et al.

(10) Patent No.: US 10,973,997 B2
(45) Date of Patent: Apr. 13, 2021

(54) NEBULIZER

(71) Applicant: Boehringer Ingelheim International GmbH, Ingelheim am Rhein (DE)

(72) Inventors: Heinrich Kladders, Muelheim-Ruhr (DE); Matthias Hausmann, Rees (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 46 days.

(21) Appl. No.: 15/411,120

(22) Filed: Jan. 20, 2017

(65) Prior Publication Data
US 2017/0209892 A1 Jul. 27, 2017

(30) Foreign Application Priority Data

Jan. 25, 2016 (EP) .................................... 16020017

(51) Int. Cl.
*A61M 11/02* (2006.01)
*A61M 11/00* (2006.01)
*A61M 15/00* (2006.01)
*B05B 11/00* (2006.01)

(52) U.S. Cl.
CPC ........... *A61M 11/02* (2013.01); *A61M 11/007* (2014.02); *A61M 15/0065* (2013.01); *B05B 11/3091* (2013.01); *A61M 15/0035* (2014.02); *A61M 2202/0468* (2013.01);
(Continued)

(58) Field of Classification Search
CPC .... A61M 11/006; A61M 11/02; A61M 15/00; A61M 16/0075; A61M 2205/071; A61M 15/0035; A61M 11/007; A61M 15/0065; A61M 2205/07; A61M 2202/0468; B05B 17/00; B05B 11/3091; B05B 11/0038; B05B 11/00412
USPC ................ 239/271, 272, 307, 337, 320–324, 239/327–329, 330–333, 345–346, 239/350–351, 355–356, 373
See application file for complete search history.

(56) References Cited

U.S. PATENT DOCUMENTS 4,162,030 A * 7/1979 Capra ................... B05B 9/0822
222/105
5,568,884 A * 10/1996 Bruna ............... A61M 15/0065
128/203.13
(Continued)

FOREIGN PATENT DOCUMENTS

EP 1818108 A1 8/2007
EP 2614848 A1 7/2013
(Continued)

OTHER PUBLICATIONS

International Search Report and Written Opinion for corresponding application PCT/EP2017/051137, dated Apr. 28, 2017.

*Primary Examiner* — Joseph A Greenlund
*Assistant Examiner* — Steven M Cernoch
(74) *Attorney, Agent, or Firm* — Matthew B. Dernier, Esq.

(57) ABSTRACT

A nebulizer for nebulizing a liquid from a container is proposed. The nebulizer comprises a liquid pump for withdrawing the liquid in doses from the container and pressurizing the respective doses for nebulization. The nebulizer comprises in addition an air pump for temporarily pressurizing the liquid in the container to help withdrawing the liquid from a collapsible bag in the container.

21 Claims, 3 Drawing Sheets

Figure 1:
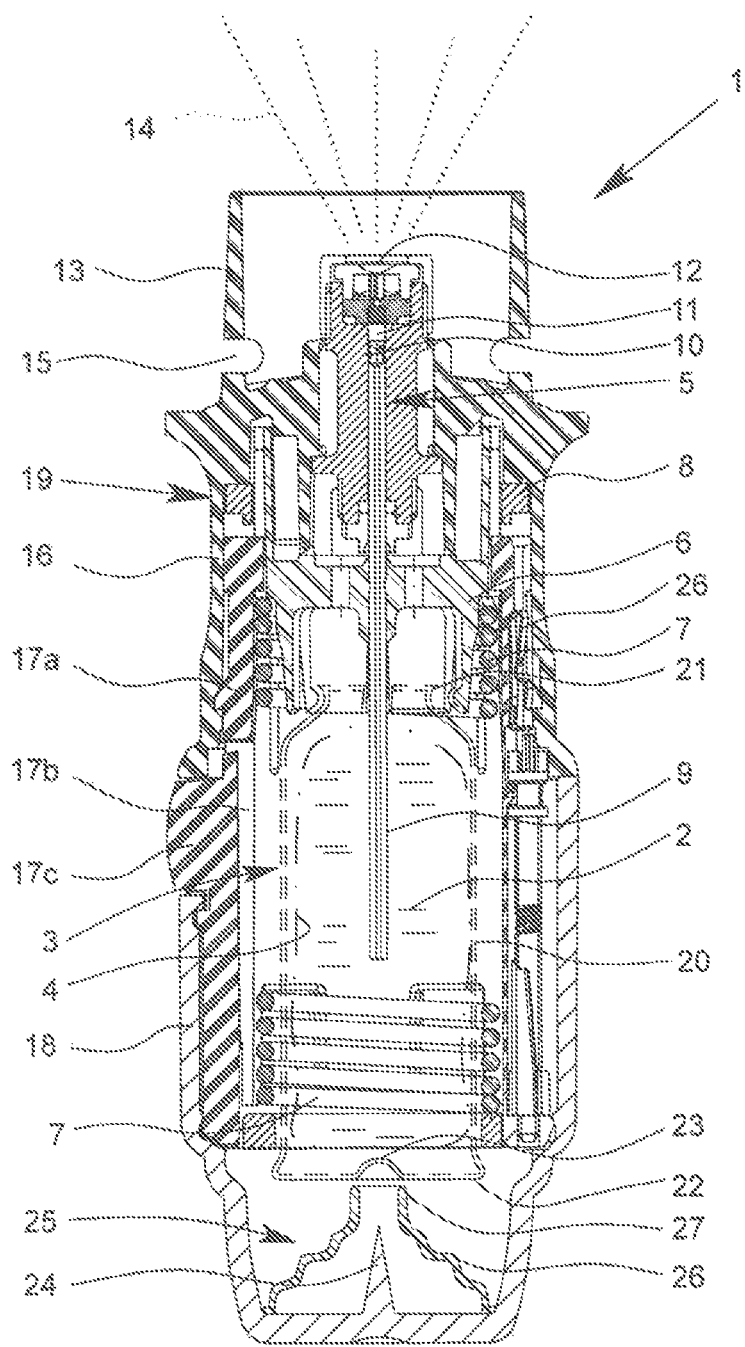

(52) U.S. Cl.
CPC ...... *A61M 2205/07* (2013.01); *B05B 11/0038* (2018.08); *B05B 11/00412* (2018.08)

(56) References Cited

U.S. PATENT DOCUMENTS

| | | | | |
|---|---|---|---|---|
| 6,094,692 | A * | 7/2000 | Kalkunte | H04L 49/90 |
| | | | | 370/232 |
| 6,938,798 | B2 | 9/2005 | Stradella | |
| 6,988,496 | B1 | 1/2006 | Eicher | |
| 6,991,041 | B2 * | 1/2006 | Laskaris | A62C 5/02 |
| | | | | 169/13 |
| 7,341,208 | B2 * | 3/2008 | Peters | B05B 1/3436 |
| | | | | 239/11 |
| 7,494,072 | B2 * | 2/2009 | Hasegawa | B05B 1/26 |
| | | | | 239/229 |
| 7,665,461 | B2 * | 2/2010 | Zierenberg | A61M 11/06 |
| | | | | 128/200.14 |
| 7,717,142 | B2 * | 5/2010 | Padar | B05B 11/00412 |
| | | | | 141/26 |
| 8,313,008 | B2 * | 11/2012 | Ciavarella | A47K 5/14 |
| | | | | 222/135 |
| 8,950,393 | B2 * | 2/2015 | Holakovsky | A61M 15/0065 |
| | | | | 128/200.14 |
| 8,960,188 | B2 * | 2/2015 | Bach | A61M 15/0065 |
| | | | | 128/200.14 |
| 2006/0016449 | A1 | 1/2006 | Eicher | |
| 2006/0027233 | A1 | 2/2006 | Zierenberg et al. | |
| 2009/0108089 | A1 * | 4/2009 | Handzel | B05B 7/241 |
| | | | | 239/8 |
| 2011/0290243 | A1 * | 12/2011 | Bach | A61M 11/006 |
| | | | | 128/200.21 |
| 2012/0090603 | A1 * | 4/2012 | Dunne | A61M 11/06 |
| | | | | 128/200.22 |
| 2017/0203056 | A1 | 7/2017 | Dunne | |

FOREIGN PATENT DOCUMENTS

| | | |
|---|---|---|
| JP | 2009538790 A | 11/2009 |
| WO | 9606011 A2 | 2/1996 |
| WO | 0049988 A2 | 8/2000 |
| WO | 2007138084 A2 | 12/2007 |
| WO | 2009047173 A1 | 4/2009 |
| WO | 2009115200 A1 | 9/2009 |
| WO | 2010094305 A1 | 8/2010 |
| WO | 2012161685 A1 | 11/2012 |
| WO | 2012162305 A1 | 11/2012 |

* cited by examiner

NEBULIZER

The present invention relates to a nebulizer.

WO 2009/047173 A2 discloses a nebulizer for nebulizing a fluid. A container can be inserted into the nebulizer. The container comprises a rigid outer casing and a bag containing multiple doses of the fluid. The container or its casing is vented so that the bag can collapse when withdrawing fluid.

WO 2010/094305 A1 discloses a nebulizer for nebulizing a fluid. A container can be inserted into the nebulizer. The container comprises a rigid outer casing and a collapsible bag containing multiple doses of the fluid. In order to avoid any undesired formation of vapor or gas bubbles in the bag when withdrawing fluid form the bag, the container can be pressurized by gas pressure in the casing to facilitate collapsing of the bag and withdrawal of fluid. However, this pressurization may lead to undesired leakage from the container during non-use, even if an additional valve is provided between the container and a pressure generator or fluid pump of the nebulizer. Further, the pressurization may significantly vary due to significant increase of the gas volume during fluid withdrawal and, thus, result in significant variation of the respectively withdrawn doses of fluid.

The container may be constructed as described in WO 96/06011 A1 or WO 00/49988 A2.

Object of the present invention is to provide a nebulizer wherein withdrawal/sucking of fluid or liquid from the container is facilitated, while undesired leakage during non-use can be prevented or minimized, and/or wherein the withdrawn drawn doses of fluid or liquid can be kept highly constant (in particular, for successive/repeated withdrawals of doses from the container) and/or precise metering is supported, and/or wherein it can be prevented the formation or growing of any gas bubble in the fluid or liquid.

The above object is achieved by a nebulizer according to claim 1. Preferred embodiments are subject of the subclaims.

The present invention relates to a nebulizer for nebulizing a fluid or liquid, preferably a liquid medicament, from a preferably replaceable container containing the fluid or liquid in particular in an inner container of variable (collapsible) volume, most preferably in a collapsible bag. Preferably, the nebulizer comprises a housing part which can be detached or opened for replacing the container. Preferably, the nebulizer comprises a liquid pump and/or pressure generator for drawing the fluid or liquid (in particular a metered dose of fluid or liquid) from the container. In particular, the container contains multiple doses of the fluid or liquid.

According to the present invention, the nebulizer comprises an air pump connectable to the container for temporarily pressurizing the fluid or liquid in the container and/or for temporarily pumping air into the container to help withdrawal of the fluid or liquid. This allows a very simple construction of the air pump separately from the container.

Preferably, the container comprises an inner container (which is flexible/collapsible, preferably in form of a collapsible bag) and a surrounding more rigid structure like a casing and/or shell. Preferably, the air pump is pneumatically connectable to a space between the casing/shell and the inner container/bag.

Preferably, the air pump pressurizes the bag of the container (or the inner container) and the fluid or liquid in the container only temporarily, in particular only when the nebulizer is cocked or tensioned or loaded (i.e. readied for nebulizing a dose of fluid) and/or when liquid is drawn out of the container. Thus, any undesired leakage of fluid from the container can be prevented or at least minimized and/or any (additional) valve between the container and the liquid pump or pressure generator of the nebulizer can be avoided. This allows a simple construction.

Further, the temporary pressurization of the fluid or bag of the container can prevent the formation or growing of any gas bubble within the fluid. This supports precise metering and/or allows minimization or reduction of the total volume of fluid initially provided in the container.

Preferably, the air pump is arranged in, fastened to or formed by the housing part of the nebulizer that can be detached or opened for inserting or replacing the container.

Preferably, the container is moveable relative to the air pump during tensioning or cocking or loading the nebulizer or withdrawing a dose of fluid from the container and/or during nebulizing or dispensing a dose of fluid. This relative container movement is preferably used for actuating the air pump and/or for only temporarily pressurizing the fluid in the container and/or only temporarily connecting the air pump to the container (preferably, the air pump is not connected to the container in a non-tensioned or non-loaded state of the nebulizer). This allows a very simple and reliable construction.

Preferably, the air pump is fluidically connectable to a bottom or axial end of the container, preferably opposite to a fluid outlet of the container and/or via a venting hole of the container. This allows a very simple construction or integration in known nebulizers.

Preferably, the air pump comprises or is formed by a bellows. This allows a very simple realization.

Figure 2:
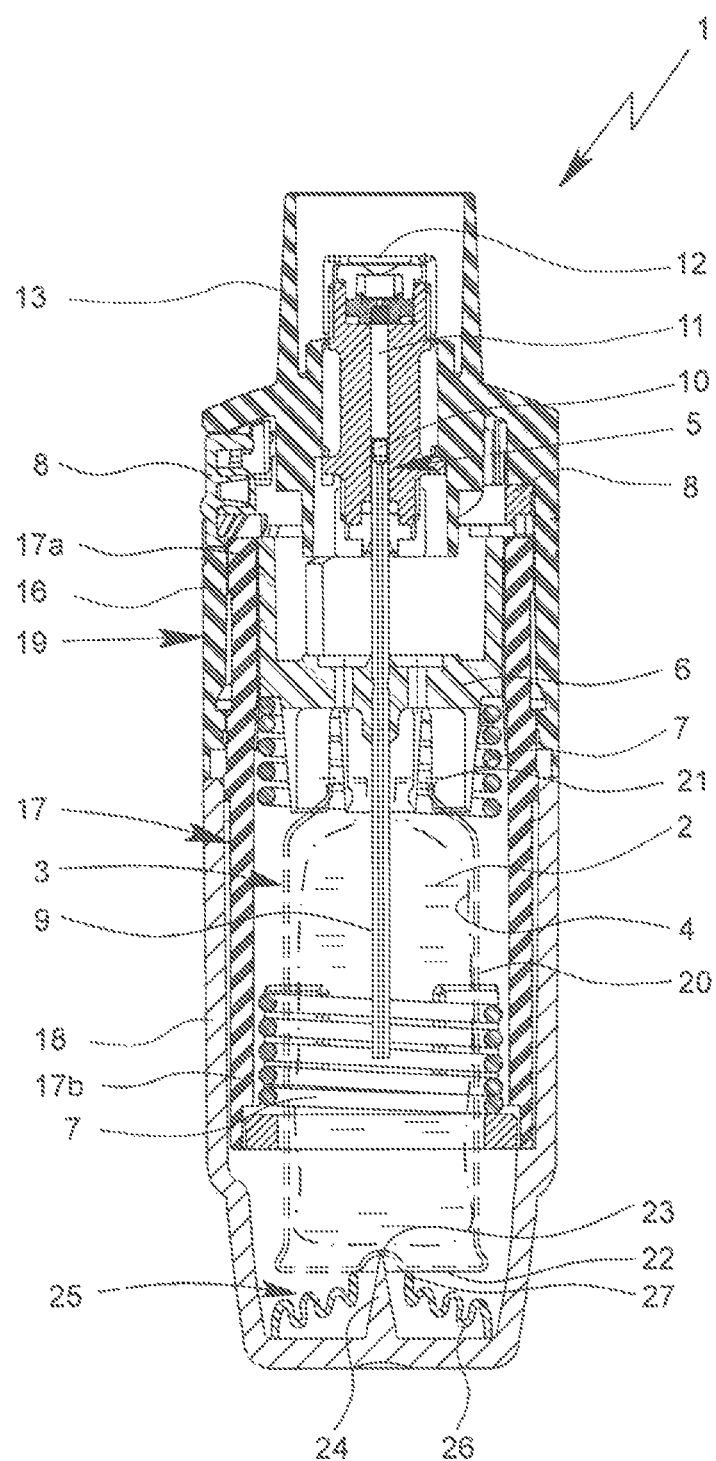
Figure 3:
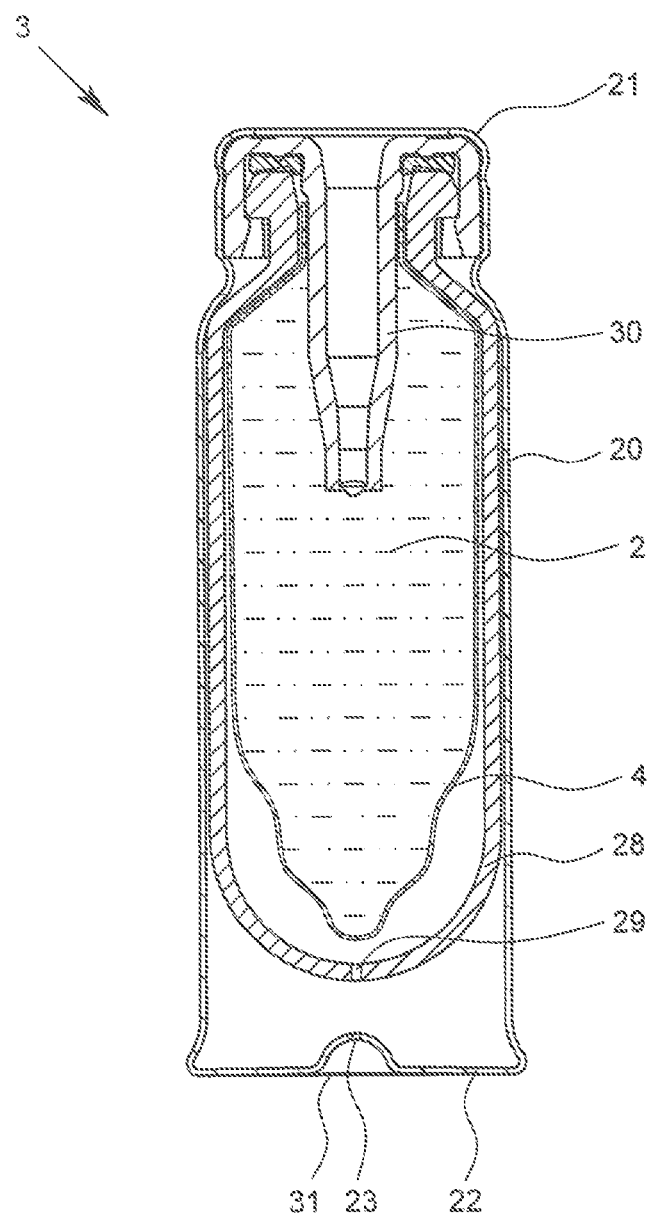

Further advantages, features, characteristics and aspects of the present invention will become apparent from the claims and the following description of a preferred embodiment with reference to the drawings. It shows:

FIG. 1 a schematic section of a nebulizer according to a preferred embodiment of the present invention in a non-tensioned state;

FIG. 2 a schematic section, rotated 90° compared with FIG. 1, of the nebulizer in a tensioned state; and FIG. 3 a schematic section of a preferred embodiment of a container of the nebulizer.

In the Figures, the same reference numerals are used for identical or similar parts, resulting preferably in corresponding or comparable properties and advantages, even if the associated description is not repeated.

FIGS. 1 and 2 show a nebulizer 1 according to the present invention for atomizing a liquid 2, particularly a highly effective pharmaceutical composition, medicament or the like, diagrammatically shown in a non-tensioned state (FIG. 1) and in a cocked or tensioned state (FIG. 2). The nebulizer 1 is constructed in particular as a portable inhaler and preferably operates only mechanical and/or propellant-free.

When the liquid 2, preferably a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises or adapted to receive an insertable or replaceable container 3 containing the liquid 2. The container 3 thus forms a reservoir for the liquid 2, which is to be nebulized.

The container 3 is shown in FIGS. 1 and 2 only schematically and in the section of FIG. 3 in more detail.

Preferably, the container 3 contains multiple doses of liquid 2 or active substance in particular sufficient to provide at least 100 or 150 and/or up to 200 or more dosage units or doses, for example, i.e. to allow at least 100 and/or up to 200 sprays or applications. The container 3 holds preferably a volume of about 0.5 to 20 ml.

Preferably, the container 3 is constructed as described in WO 96/06011 A2 and/or WO 00/49988 A2.

Further, the number of doses contained in the container 3 and/or the total volume of the liquid 2 contained in the container 3 can vary depending on the liquid 2 or respective medicament and/or depending on the container 3 and/or depending on the necessary medication or the like.

Preferably, the nebulizer 1 is adapted to nebulize a dose of 1 to 50 microliters of liquid 2, even more preferably a dose of 5 to 20 microliters, within one actuation/use of the nebulizer 1/within one spray/aerosol delivery/dispension.

Preferably, the container 3 can be replaced or exchanged, wherein the total number of uses of the nebulizer 1 and thus the number of containers 3, which can be used with the same nebulizer 1, is preferably restricted, e.g. to a total number of four, five or six containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired.

The container 3 is preferably of rigid construction, the liquid 2 in particular being held in a (flexible) inner container of variable volume, preferably a collapsible bag 4 in the container 3. In particular, the container 3 comprises a rigid casing 20, a fluid outlet or head 21 and/or a base 22. Preferably, the container 3, casing 20 or base 22 is provided with a venting opening or hole 23 which is opened before or during first use.

Preferably, the container 3 comprises in addition to the outer, preferably metallic casing 20 an inner, preferably rigid shell 28. The shell 28 encompasses or surrounds the bag 4.

The shell 28 is preferably made of plastics and/or extends up to the outlet or head 21.

Preferably, the shell 28 is rigidly fastened or received within the casing 20. However, other constructional solutions are possible as well.

The bag 4 is received preferably within the shell 28 such that it can collapse within the shell 28 when liquid 2 is withdrawn. FIG. 3 shows an intermediate state with already partially withdrawn liquid 2, i.e. with partially collapsed bag 4 in a very schematic section.

The container 3 or bag 4 is preferably closed by a closure 30 as schematically shown in FIG. 3. It has to be noted that the container 3 or closure 30 is still closed in FIG. 3, in particular the conveying element or tube 9 has not been inserted yet.

Further, the FIG. 3 shows the container 3 with still closed venting. In particular, a seal 31, such as a foil or the like, covers or seals the base 22 or venting hole 23 of the container 3 or its casing 20. However, other constructional solutions are possible as well.

When the venting, in particular the seal 31, is open, air or any other gas can flow through the venting hole 23 into casing 20 and through venting opening 29 into shell 28 so that pressure equalisation is possible or achieved. In particular, negative air pressure can be avoided or at least compensated when withdrawing liquid 2 and, thus, collapsing bag 4. However, a throttle effect of the venting hole 23 and venting opening 29 may have different impact on the temporary pressure differences occurring during fluid withdrawal which might result in some variation of the volume of withdrawn doses and/or might even result in the formation or growing of any gas bubble in the liquid 2/bag 4. The present invention can minimize or avoid any such effects due to temporarily pressurizing the liquid 2 and/or temporarily pumping air into the container 3 as described later in detail.

The nebulizer 1 comprises a delivery mechanism, preferably a pressure generator or liquid pump 5, for conveying and nebulizing the liquid 2, particularly in a preset and optionally in an adjustable dosage amount. In particular, the pressure generator or liquid pump 5 withdraws or sucks liquid 2, namely a dose of the liquid 2, from the container 3 or its bag 4, preferably when cocking or tensioning or loading the nebulizer 1. Then, the withdrawn liquid 2 or dose of liquid 2 is dispensed, in particular pressurized and/or nebulized, preferably in a second step after the tensioning or loading process. In particular, the nebulizer 1 comprises an energy store (preferably a drive spring 7) which is loaded (preferably tensioned) during the loading or tensioning process and the energy is released for nebulizing the liquid 2 or dose of liquid 2 which has been drawn into the nebulizer 1 during the tensioning or loading process. Thus, the normal use of the preferred nebulizer (1) encompasses the loading process and the dispensing process.

The nebulizer 1 or pressure generator/liquid pump 5 comprises preferably a holder 6 for holding the container 3, a drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator/liquid pump 5 comprises preferably a conveying element, such as a conveying tube 9, a non-return valve 10, a pressure chamber 11 and/or a nozzle 12 for nebulizing the liquid 2 into a mouthpiece 13.

The completely inserted container 3 is fixed or held in the nebulizer 1 via the holder 6 such that the conveying element fluidically connects the container 3 or its bag 4 to the nebulizer 1 or pressure generator/liquid pump 5. Preferably, the conveying tube 9 penetrates into the container 3 and/or bag 4.

The nebulizer 1 or holder 6 is preferably constructed so that the container 3 can be released or exchanged.

When the drive spring 7 is axially tensioned in the tensioning process or during cocking, the holder 6 with the container 3 and the conveying tube 9 are moved downwards in the drawings and liquid 2 is withdrawn or sucked out of the container 3 into the liquid pump 5 or its pressure chamber 11 through the non-return valve 10. In this state, the holder 6 is caught by the blocking element 8 so that the drive spring 7 is kept compressed. Then, the nebulizer 1 is in the cocked or tensioned state.

During the subsequent relaxation in the dispensing or nebulization process after actuation or pressing of the blocking element 8, the liquid 2 in the pressure chamber 11 is put under pressure as the conveying tube 9 with its now closed non-return valve 10 is moved back in the pressure chamber 11, here in the drawings upwards, by the relaxation or force of the drive spring 7 and now acts as a pressing ram or piston. This pressure forces the liquid 2 through the nozzle 12, whereupon it is nebulized into the aerosol 14, as shown in FIG. 1, and, thus, dispensed.

Generally, the nebulizer 1 operates with a spring pressure of 5 to 300 MPa, preferably 10 to 250 MPa on the liquid 2, and/or with a volume of liquid 2 delivered per stroke of 10 to 50 μl, preferably 10 to 20 μl, most preferably about 15 μl.

The liquid 2 is converted into or nebulized as aerosol 14, the droplets of which have an aerodynamic diameter of up to 20 µm, preferably 3 to 10 µm. Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while air can be sucked into the mouthpiece 13 through at least one optional air supply opening 15.

The nebulizer 1 comprises preferably a housing 19 and/or (upper) housing part 16 and optionally a biasing or inner part 17 preferably which is rotatable relative thereto (FIG. 2) and/or has an upper part 17a and a lower part 17b (FIG. 1).

The nebulizer 1 or housing 19 comprises preferably a (lower) housing part 18. This part 18 is in particular manually operable, and/or releasable fixed, particularly fitted or held onto the inner part 17, preferably by means of a retaining element 17c.

Preferably, the housing parts 16 and 18 and/or other parts form the housing 19 of the nebulizer 1.

In order to insert and/or replace the container 3, preferably the housing 19 can be opened and/or the housing part 18 can be detached from the nebulizer 1, inner part 17 or housing 19.

Generally and preferably, the container 3 can be inserted before the housing 19 is closed and/or before the housing part 18 is connected to the housing 19. The container 3 may be inserted, opened and/or fluidically connected to the delivery mechanism or liquid pump 5 automatically or simultaneously when (completely) connecting the housing part 18 to the housing 19/nebulizer 1 and/or when (completely) closing the housing 19/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation or rotation of an actuation member, here preferably by rotating housing part 18 or any other component.

The actuation member, preferably the housing part 18, can be actuated, here rotated relative to the upper housing part 16, carrying with it or driving the inner part 17. The inner part 17 acts on a gear or transmission to transform the rotation in an axial direction. As a result the drive spring 7 is tensioned in the axial direction by means of the gear or transmission (not shown) formed between the inner part 17, in particular its upper part 17a, and the holder 6 and acting on the holder 6. During tensioning the container 3 and holder 6 are moved axially downwards until the container 3 assumes an end position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus the container 3 executes a lifting or stroke movement during the tensioning process and during the nebulizing process.

The housing part 18 preferably forms a cap-like lower housing part and/or fits around or over a lower free end portion of the container 3. As the drive spring 7 is tensioned the container 3 moves with its end portion or base 22 (further) into the housing part 18 or towards the end face thereof, while an aeration means, such as a piercing element 24 arranged in the housing part 18, comes in contact with the base 22 or venting hole 23 of the container 3 and opens or pierces the container 3 or a seal or foil thereon when the container 3 makes contact with it for the first time, to allow air in or aeration, preferably by opening or piercing venting hole 23. The venting hole 23 allows for pressure compensation inside the container 3 when liquid 2 is drawn from the container 3 during the tensioning of the nebulizer 1.

The nebulizer 1 comprises an air pump 25 for temporarily pressurizing the liquid 2 in the container 3, in particular the bag 4 in the container 3, preferably to help collapsing the bag 4 and/or to facilitate withdrawal or sucking of liquid 2 from the container 3.

The air pump 25 is formed preferably separately from the container 3.

The air pump 25 is preferably connectable—in particular only temporarily—to the container 3 or its casing 20 or base 22 or venting hole 23.

The air pump 25 is preferably arranged opposite to the liquid pump 5 and/or the fluid outlet or head 21 of the container 3.

The air pump 25 is arranged or located preferably at or in the housing part 18 and/or adjacent to the base 22 of the container 3.

Preferably, the air pump 25 comprises or is formed by a bellows 26.

Preferably, the air pump 25 or bellows 26 comprise a connecting portion 27 for pneumatically connecting the air pump 25 or bellows 26 to the container 3. Preferably, the connecting portion 27 is tube-like and/or can abut against the container base 22 to form a pneumatic connection to the aeration or venting hole 23. However, other constructional solutions are possible as well.

Preferably, the pump body or bellows 26 is formed from an elastic and/or elastomeric material.

Preferably, the connecting portion 27 comprises or forms a sealing, such as a flexible lip, an elastic portion or the like, cooperating with the container base 22 or any other part of the container 3 for forming a (temporary) gas connection between the pump 25 and container 3. However, other constructional solutions are possible as well.

The air pump 25 or bellows 26 is preferably actuated by the movement of the container 3 within the nebulizer and/or the stroke-like movement or tensioning movement of the container 3.

In particular, the container 3 or its base 22 is spaced from the air pump 25 or bellows 26 or its connecting portion 27 when the nebulizer 1 or container 3 is in the non-tensioned state or after nebulizing a dose.

Thus, the air pump 25 or bellow 26 is temporarily open and/or disconnected from the container 3 or vice versa. In particular, the aeration or venting hole 23 is open or uncovered in the non-tensioned state so that free compensation is possible between the pressure within the container casing 20 and the outer atmosphere.

Preferably, the stroke-like movement or tensioning movement of the container 3 controls opening or filling of the pump 25.

When tensioning the nebulizer 1, the container 3 is moving towards and/or relative to the air pump 25 or its connecting portion 27. After a first (shorter) part of the tensioning movement, the container 3 or its base 22 (pneumatically) connects with the air pump 25 or its connecting portion 27. During the further or second (larger) part of the tensioning movement, the air pump 25 or bellows 26 is actuated or compressed so that an air pressure is generated which can directly act—here preferably via the connecting portion 27 and the venting hole 23—on the liquid 2 in the container 3 or, more precisely, on the bag 4 (i.e. the flexible inner container) within the container 3. In other words, the air pump 25 pumps air into the space which is between the bag 4 and the casing 20/shell 29 at the end of the tensioning process.

Preferably, the air pump 25 or bellows 26 comprises a total volume and/or a pump volume of more than 0.1 cm$^3$, in particular of more than 0.2 cm$^3$, and more preferably of more than 0.3 cm$^3$.

Preferably, the pump volume of the air pump 25, i.e. here the volume difference between the uncompressed state and the compressed state of the air pump 25 and/or the minimum volume of air pumped into the container 3 by the air pump 25 during each actuation, is more than 3%, in particular more than 5%, most preferably more than 8%, and/or less than 50%, preferably less than 40%, most preferably less than 25%, of the air volume of the container 3 after withdrawing the medium or maximum number of doses of liquid 2.

Preferably, the air pump 25 or bellows 26 provides a pressure increase in the container 3 (in particular in the space between the inner container and the casing 20 and/or shell 28) or acting on the liquid 2/bag 4 of more than 25 hPa, preferably more than 40 hPa, and most preferably of more than 50 hPa, in particular just after tensioning the nebulizer 1.

The pressure increase mentioned above depends on the state of collapsing of the bag 4. The above values apply in particular when the bag 4 is completely collapsed and/or when the maximum number of withdrawn doses of liquid 2 is reached.

The pressure acting on the bag 4 in the container 3 increases during the second part of the tensioning movement of the container 3, i.e. during the actuation of the air pump 25, until the tensioned state or end position is reached. This pressure increase helps of facilitates withdrawal or sucking of liquid 2 from the container 3 or its bag 4.

Preferably, the pressure decreases again, in particular automatically, during the nebulization process (preferably due to expansion of the air pump 25 or bellows 26 or due to disconnection of the air pump 25 or connecting portion 27 from the container 3 during the nebulization movement of the container 3) and/or even in the tensioned state (preferably due to air leakage in particular between the connecting portion 27 and the container base 22).

Therefore, the bag 4 or liquid 2 is compressed or pressurized only temporarily in the container 3, preferably mainly only during the tensioning movement and/or preferably primarily only during withdrawal of a dose of liquid 2 from the container 3 or its bag 4.

After withdrawing or sucking liquid 2 from the container 3 or its bag 4, the nebulizer 1 is in the tensioned or cocked state and/or is ready for dispensing/nebulization.

After actuating or firing the nebulizer 1, preferably by actuating or pressing element 8, the pressure generator or liquid pump 5 pressurizes and dispenses the previously withdrawn dose of the liquid 2 while the container 3 is moving in opposite direction and finally retracting from the air pump 25 and/or its connecting portion 27.

The pump 35 may be provided or connected with a check valve (not shown) allowing re-filling of the pump 25 and/or preventing any under-pressure in the pump 25, e.g. during the dispensing or actuation stroke of the nebulizer 1 so that any negative influence of the pump 25, such as a holding force acting opposite to the dispensing movement of the container 3, is securely prevented.

The air pump 25 works preferably mechanically.

Preferably, the piercing element 24 is integrated into or located within the air pump 25 or bellows 26.

In particular, the air pump 25 and the piercing element 24 and/or housing part 18 may form one assembled or unitary component.

Preferably, the air pump 25 is arranged in the center of the nebulizer 1 and/or below the container 3 and/or axially aligned with the nebulizer 1 and/or container 3.

Preferably, the air pump 25 or its bellows 26 comprises an essentially pyramidal or conical or truncated form pointing towards the container 3 or its base 22. However, other constructal solutions and geometrical forms are possible as well.

Preferably, the bellows 26 comprises folds which are arranged concentrically and/or comprise different diameters and/or are reduced in diameter towards the container 3 and/or fold alternatively in axial direction.

The present invention allows, supports or ensures a very precise metering and/or facilates to keep the volume of the dispensed doses highly constant. Further, it can be prevented the formation or growing of any gas bubble within the liquid 2 or bag 4. This allows also a minimization or reduction of the total volume of liquid 2 initially provided in the container 3 even if a very high number of doses such as 100 or 150 doses or more are provided.

Individual features, aspects and/or principles of the embodiment described may also be combined with one another as desired and may be used particularly in the shown nebulizer 1, but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers or in other devices for the delivery of liquid formulations.

Preferably, the liquid 2 is, as already mentioned, especially an aqueous pharmaceutical formulation or an ethanolic pharmaceutical formulation. However, it may also be some other pharmaceutical formulation, a suspension or the like. Preferably, the expression liquid is to be broadly understood to encompass fluids containing liquid, such as suspensions, suslutions, liquefied formulations and the like.

Preferred ingredients and/or formulations of the preferably medicinal liquid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

| List of reference numerals | |
| --- | --- |
| 1 | nebulizer |
| 2 | liquid |
| 3 | container |
| 4 | bag |
| 5 | pressure generator/liquid pump |
| 6 | holder |
| 7 | drive spring |
| 8 | blocking element |
| 9 | conveying tube |
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner part |

-continued

| List of reference numerals | |
|---|---|
| 17a | upper part of inner part |
| 17b | lower part of inner part |
| 17c | retaining element |
| 18 | housing part (lower part) |
| 19 | nebulizer housing |
| 20 | casing |
| 21 | head |
| 22 | base |
| 23 | venting hole |
| 24 | piercing element |
| 25 | air pump |
| 26 | bellows |
| 27 | connecting portion |
| 28 | shell |
| 29 | venting opening |
| 30 | closure |
| 31 | seal |

The invention claimed is:

1. A nebulizer (1) for nebulizing a liquid (2), comprising:
a nozzle (12);
a replaceable container (3) having an inner container of variable volume containing multiple doses of the liquid (2), and including a fluid output (21);
a liquid pump (5) for withdrawing a dose of the liquid (2) from the fluid output (21) of the replaceable container (3), pressurizing the dose outside the replaceable container (3) for nebulization, and driving the dose through the nozzle (12) during an actuation stroke;
a housing (18, 19) openable for inserting or replacing the replaceable container (3); and
an air pump (25) operatively connectable to the replaceable container (3) to urge a reduction in the variable volume of the inner container in order to pressurize the liquid (2) inside the replaceable container (3) during specific periods of time to help urge the liquid (2) to exit in doses from the inner container of the replaceable container (3), wherein:
during the specific periods of time during which the air pump (25) pressurizes the liquid (2) inside the replaceable container (3), the liquid pump (5) does not pressurize the dose outside the replaceable container (3) for nebulization, and
during times at which the liquid pump (5) pressurizes the dose outside the replaceable container (3) for nebulization, the air pump (25) does not pressurize the liquid (2) inside the replaceable container (3) and the air pump (25) physically disconnects from the replaceable container (3) during the actuation stroke.

2. The nebulizer according to claim 1, wherein the air pump (25) is arranged in and/or attached to the housing (18).

3. The nebulizer according to claim 1, wherein the air pump (25) is connectable to an outer casing (20) of the replaceable container (3), to a container base (22) and/or to a venting hole (23) of the replaceable container (3) or an outer casing (20) thereof.

4. The nebulizer according to claim 1, wherein during the use of the nebulizer (1), the air pump (25) is only intermittently in pneumatic connection with the replaceable container (3).

5. The nebulizer according to claim 1, wherein the replaceable container (3) is moveable axially in the nebulizer (1) when withdrawing a dose of liquid (2) and/or when pressurizing or dispensing a dose of the liquid (2).

6. The nebulizer according to claim 5, wherein the air pump (25) is actuated by a relative movement of the replaceable container (3) within the housing (18, 19) of the nebulizer (1).

7. The nebulizer according to claim 6, the relative movement of the replaceable container (3) within the housing (18, 19) controls an intermittent pneumatic connection of the replaceable container (3) to the air pump (25).

8. The nebulizer according to claim 1, wherein the air pump (25) comprises or is formed by a bellows (26).

9. The nebulizer according to claim 1, wherein the air pump (25) or a bellows (26) thereof is axially and/or elastically compressible.

10. The nebulizer according to claim 1, wherein the air pump (25) pressurizes when tensioning or loading the nebulizer (1) and the liquid pump (5) pressurizes when dispensing or nebulizing a dose of liquid (2).

11. The nebulizer according to claim 1, wherein the nebulizer (1) and replaceable container (3) are adapted to provide more than 100 doses of the liquid (2).

12. The nebulizer according to claim 1, wherein the air pump (25) is adapted to generate an intermittent pressure increase of more than 25 hPa.

13. The nebulizer according to claim 1, wherein the air pump (25) is adapted to generate an intermittent pressure increase of more than 40 hPa.

14. The nebulizer according to claim 1, wherein the air pump (25) is adapted to generate an intermittent pressure increase of more than 50 hPa.

15. The nebulizer (1) of claim 1, wherein the replaceable container (3) includes a rigid portion within which a collapsible bag (4) containing the liquid (2) is disposed, the fluid output (21), a base (22), and a venting hole (23) through the rigid portion (20, 28) of the replaceable container (3); and the air pump (25) intermittently pneumatically connects to the base (22) of the replaceable container (3) for intermittently pressurizing a space between the rigid portion (20, 28) and the collapsible bag (4) of the replaceable container (3) to help urge the liquid (2) to exit the collapsible bag (4) in doses from the replaceable container (3).

16. The nebulizer according to claim 15, wherein the air pump (25) comprises a tube connection portion (27) for intermittently connecting to the base (22) of the replaceable container (3).

17. The nebulizer according to claim 15, wherein the air pump (25) or a connecting portion (27) thereof is axially spaced from the base (22) of the replaceable container (3) when the nebulizer (1) is non-tensioned or after dispensing a dose of liquid (2).

18. The nebulizer according to claim 15, wherein the air pump (25) or a connecting portion (27) thereof comprises or forms a seal (31) cooperating with or abutting against the base (22) of the replaceable container (3) on an intermittent basis.

19. The nebulizer according to claim 15, wherein the rigid portion of the replaceable container (3) comprises a shell (28) within which the collapsible bag (4) is disposed, and an outer casing (20) within which the shell (28) is disposed.

20. The nebulizer according to claim 19, wherein the air pump is pneumatically connectable to a space between the collapsible bag (4) and the casing (20) and/or a space between the collapsible bag (4) and the shell (28).

21. The nebulizer according to claim 15, wherein the air pump (25) intermittently pneumatically connects to the venting hole (23) of the replaceable container (3) and delivers air through the venting hole (23) into the space between the rigid portion (20, 28) and the collapsible bag (4) of the replaceable container (3).

\* \* \* \* \*